(12) United States Patent
Li et al.

(10) Patent No.: US 11,573,339 B2
(45) Date of Patent: Feb. 7, 2023

(54) TIMING CALIBRATION USING INTERNAL RADIATION AND EXTERNAL RADIATION SOURCE IN TIME OF FLIGHT POSITRON EMISSION TOMOGRAPHY

(71) Applicant: CANON MEDICAL SYSTEMS CORPORATION, Otawara (JP)

(72) Inventors: Xiaoli Li, Vernon Hills, IL (US); Yi Qiang, Vernon Hills, IL (US); Kent C. Burr, Vernon Hills, IL (US); Peng Peng, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/907,972

(22) Filed: Jun. 22, 2020

(65) Prior Publication Data
US 2021/0199823 A1 Jul. 1, 2021

Related U.S. Application Data

(60) Provisional application No. 62/955,270, filed on Dec. 30, 2019.

(51) Int. Cl.
*G01T 7/00* (2006.01)
*G01T 1/29* (2006.01)
*A61B 6/00* (2006.01)
*A61B 6/03* (2006.01)

(52) U.S. Cl.
CPC .............. *G01T 7/005* (2013.01); *A61B 6/037* (2013.01); *A61B 6/5258* (2013.01); *G01T 1/2985* (2013.01)

(58) Field of Classification Search
CPC ...... A61B 6/037; A61B 6/5256; A61B 6/5258; G01T 7/005; G01T 1/2985
See application file for complete search history.

(56) References Cited

U.S. PATENT DOCUMENTS

| | | | | |
|---|---|---|---|---|
| 2015/0301201 | A1* | 10/2015 | Rothfuss | ............. G01T 1/40 250/252.1 |
| 2016/0299240 | A1* | 10/2016 | Cho | ............. G01T 7/005 |

(Continued)

FOREIGN PATENT DOCUMENTS

JP 2014-228551 12/2014

OTHER PUBLICATIONS

Leroux et al. Time discrimination techniques using artificial neural networks for positron emission tomography, IEEE Transactions on Nuclear Science, vol. 56, No. 3, pp. 588-595 (Year: 2009).*

(Continued)

*Primary Examiner* — David P Porta
*Assistant Examiner* — Fani Polyzos Boosalis
(74) *Attorney, Agent, or Firm* — Oblon, McClelland, Maier & Neustadt, L.L.P.

(57) ABSTRACT

A method and system for providing improved timing calibration information for use with apparatuses performing Time of Flight Positron Emission Tomography scans. Relative timing offset, including timing walk, within a set of processing units in the scanner are obtained and corrected using a stationary limited extent positron-emitting source, and timing offset between the set of processing units is calibrated using an internal radiation source, for performing calibration.

18 Claims, 15 Drawing Sheets

(56) References Cited

U.S. PATENT DOCUMENTS

2017/0276811 A1    9/2017   Wang et al.
2020/0072988 A1    3/2020   Cho et al.

OTHER PUBLICATIONS

Sanders Medical Products Nuclear Medicine Calibration Source Model PET-XXX/YY, 7 pages (Year: 2015).*
Li, et al., "Timing Calibration for Time-of-Flight PET Using Position-Emitting Isotopes and Annhlation Targets", https://ieeexplore.ieee.org/document/7471623, May 18, 2016.
H. Rothfuss, A. Moor, J. Young, V. Panin and C. Hayden, "Time alignment of time of flight positron emission tomography using the background activity of LSO," 2013 IEEE Nuclear Science Symposium and Medical Imaging Conference (2013 NSS/MIC), Seoul, 2013, pp. 1-3, doi: 10.1109/NSSMIC.2013.6829400.
Extended European Search Report dated May 28, 2021 in European Patent Application No. 20217642.6, 8 pages.

* cited by examiner

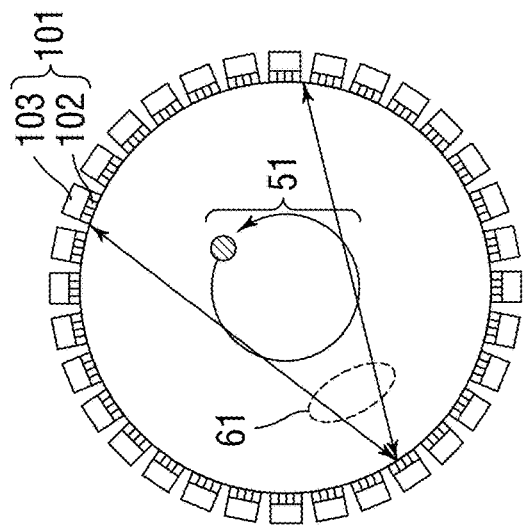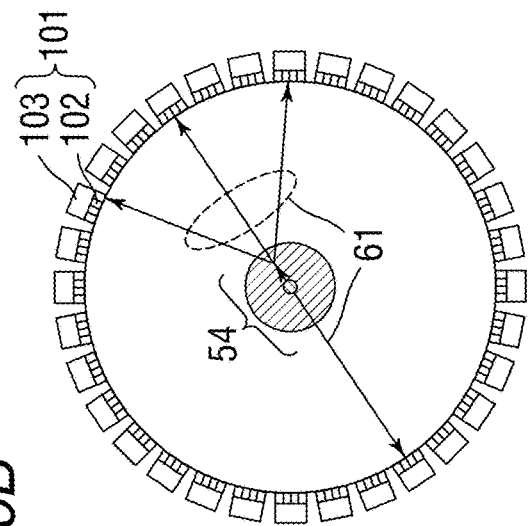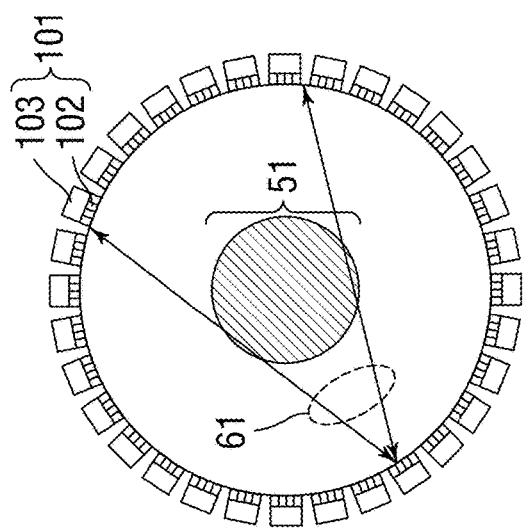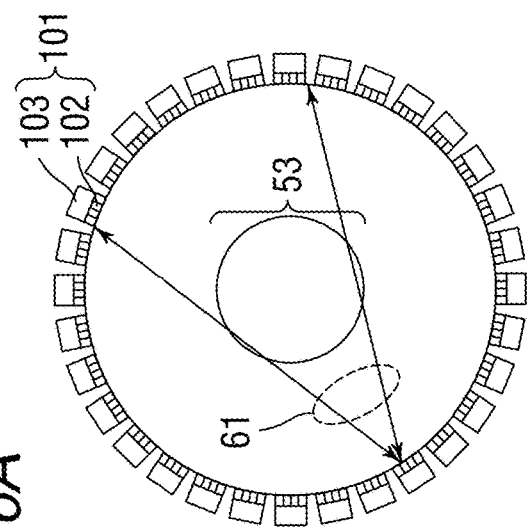

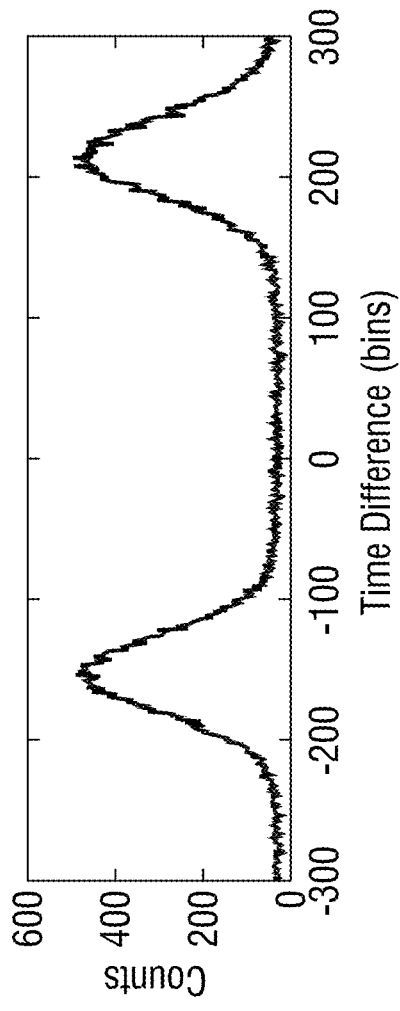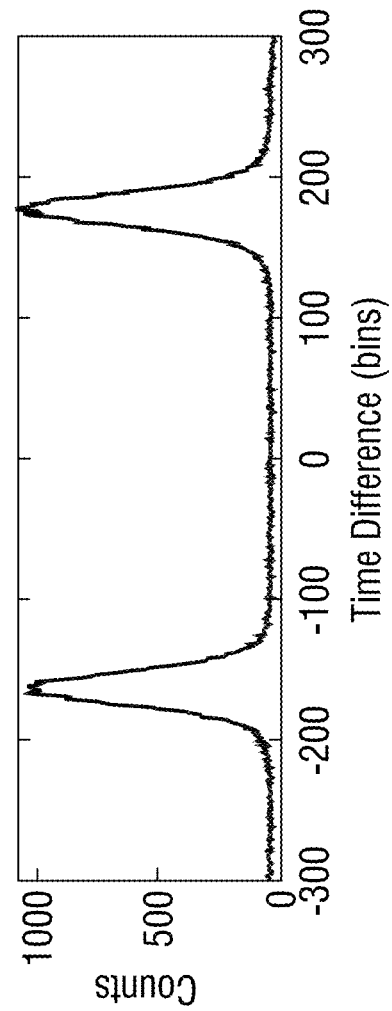
FIG. 8A
FIG. 8B

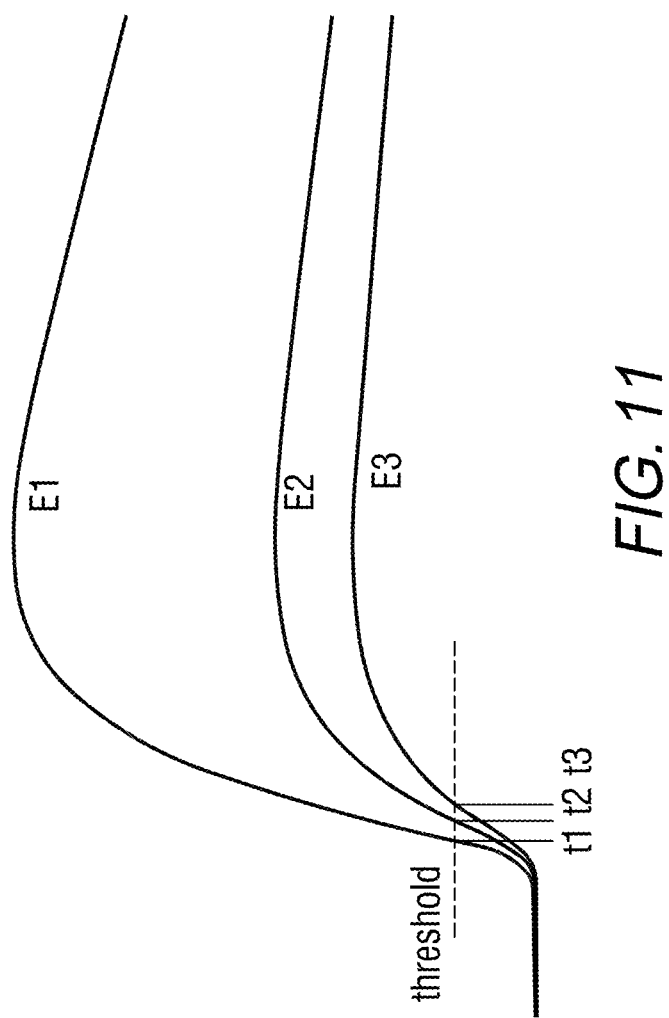

TIMING CALIBRATION USING INTERNAL RADIATION AND EXTERNAL RADIATION SOURCE IN TIME OF FLIGHT POSITRON EMISSION TOMOGRAPHY

This application is based on and claims the benefit of and priority to U.S. Provisional Patent Application No. 62/955,270, entitled "TIMING CALIBRATION USING LUTETIUM BACKGROUND RADIATION AND EXTERNAL RADIATION SOURCE", filed on Dec. 30, 2019, the entire contents of which are herein incorporated by reference.

BACKGROUND

Technical Field

The disclosure relates to a method and system for providing improved timing calibration information for use with apparatuses for performing Time of Flight (TOF) positron emission tomography (PET) scans, and, in one embodiment, to a TOF PET scan using an internal radiation source (e.g., a lutetium radiation source) in conjunction with a stationary limited extent annihilation radiation source (e.g., a positron emitting Ge68/F18-FDG line source) for performing calibration thereof.

Description of the Related Art

In PET, images of a living body are created. PET scanners produce images that illustrate various biological processes and functions. Typically, in a PET scan, the patient is initially injected with a radioactive substance known as a PET isotope. The injected PET isotope can act as a tracer when it becomes involved in certain physiological processes in the patient's body. Typical positron-emitting PET isotopes include $^{11}$C, $^{13}$N, $^{15}$O and $^{18}$F. When positrons (along with neutrons) are emitted from an unstable nucleus within the body, they combine with electrons in the neighboring tissues and become annihilated. The annihilation event results in a pair of gamma photons being released in opposite directions. The gamma photons are then detected by a detector ring like the one shown in FIG. 1. The detector ring 300 may comprise a number of detectors (e.g., 101) each having a scintillator block and a photo sensor. For example, detector 101 comprises a scintillator block 102 and a photo sensor 103.

One aspect of PET detection is TOF PET, where the arrival time of a pair of coincident photons is measured. In TOF PET, upon detection of a radiation event (e.g., a gamma photon), the scintillator block at the detection locale time-stamps the detected radiation event. Incorporation of the arrival time gives more weight to the more probable locations of the emission point for each event, thereby reducing statistical uncertainty in the reconstructed images.

In PET, each detector assigns an energy and a time stamp to each detected gamma ray. An energy window is applied to select energies within a range surrounding 511 keV, and a coincidence timing window is applied to determine coincident pairs of gamma rays. Each coincident pair defines a line-of-response (LOR) connecting the two detector elements which detected the gamma rays. Reconstruction methods are applied to produce an image from the detected LORs.

In TOF PET, the difference in the time stamps of each gamma ray in the coincident pair is used to preferentially add more weight to the more probable locations of the annihilation point for each event, thereby reducing statistical uncertainty in the reconstructed images. In order to provide a significant improvement to the reconstructed images, the measured time difference recorded for each LOR must be very accurate, typically with accuracy in the range of a few hundred picoseconds. Due to unavoidable manufacturing tolerances such as differences in cable lengths or timing response of different photo sensors in the detectors, calibration is required to ensure sufficient accuracy of the measured time differences.

One approach could be to individually calibrate the time difference for each LOR in the system. However, since PET scanners typically contain tens of thousands of detector elements, and the number of LORs is on the order of hundreds of millions, this approach is not practical. The common approach in the conventional art is to perform an offset correction for each detector element. For each detector element, an offset correction value is added to the measured time stamp for that element before determining whether the detected gamma ray is part of a coincident pair. The offset correction values for the two gamma rays in the coincident pair are also applied when calculating the TOF difference for the pair for use in reconstruction. Generally, a timing offset value is a "signed" value, meaning that it can be positive or negative.

For a TOF PET system, where timing differences are measured, if there are N detector elements in the system, to be able to accurately measure timing differences, (N−1) timing offset values will need to be determined. For example, the timing offset value for one element could be arbitrarily set to zero, and the other (N−1) offset values could be determined relative to the one element that was arbitrarily set to zero. Alternatively, N offset values could be calculated with the additional constraint that the average offset value for all N detector elements is zero (meaning that there are again only (N−1) independent values). Thus, any measured timing difference will not change if the same additional timing offset value is added to all measurements.

Some non-limiting examples illustrating the above are presented below. These examples are for illustration only, and are not necessarily representative of preferred embodiments of clinical PET systems.

Consider the example of a source of annihilation radiation 50 placed between two detector elements D10 and D30, as shown in FIG. 2A. Coincident events produce one LOR 60 between the detector elements. In this example, the annihilation radiation source 50 is placed equidistant from D10 and D30 (choices other than equidistant are equally valid). The time measured by D10 is designated by $t_{D10}$, and the time measured by D30 designated by $t_{D30}$. Noise or uncertainty in the time measurements will produce a distribution of time differences ($t_{D10} - t_{D30}$) which can be plotted as a histogram, as shown in FIG. 2B. Prior to calibration, the measured histogram 70 has a mean value of $t_{measured}$ (this could be calculated as a simple average, or it could be determined, for example, by a least-squares fit of a Gaussian function to the measured histogram). Since the source is equidistant from the two detectors, the time of flight to the two detectors is equal and the expected time difference is zero. The measurements of the time difference distribution allow us to write a single equation $$(t_{D10} + t_{OffsetD10}) - (t_{D30} + t_{OffsetD30}) = t_{measured} + t_{OffsetD10} - t_{OffsetD30} = 0$$

where $t_{OffsetD10}$ and $t_{OffsetD30}$ are the offset correction values for D10 and D30, respectively. Since there is only one equation and two unknowns, another constraint needs to be applied in order to be able to determine $t_{OffsetD10}$ and $t_{OffsetD30}$. One could choose $t_{OffsetD10}=0$, resulting in $t_{OffsetD30}=t_{measured}$. Or, one could choose $(t_{OffsetD10}+t_{OffsetD30})/2=0$, resulting in $t_{OffsetD10}=-t_{measured}/2$ and $t_{OffsetD30}=t_{measured}/2$. Either of these two choices (or any of many other possible choice of constraints) results in a corrected timing histogram 80 which is centered at the expected value (zero). In this simple example, with two detectors (i.e. N=2), one is able to determine one (i.e. N−1) independent offset value in order to be able to calibrate the system to accurately measure the timing difference (i.e. TOF).

If the number of detectors was increased to four, and an annihilation radiation source is placed between and equidistant from the detectors, then two LORs are created, resulting in two equations, one for each of the measured mean time differences for the LORs. With N=4 detectors, for a full timing calibration, three (N−1=3) independent offset values need to be determined. Determining three unknowns from two equations is clearly impossible. This indicates a substantial problem with performing a timing calibration with a single limited-extent source in a single fixed position.

One way to solve this problem is sketched in FIG. 3. A second source 55 has been placed equidistant from and between detectors D30 and D40 (again, the choice of equidistant is made to make the illustration simple; it is not a necessary choice). This second source produces an additional LOR 65, allowing to write a third equation relating the timing offset values to each other. Having three equations with three unknowns enables to solve for the three (N−1=3) independent timing offset values that are required to fully calibrate the timing response of the system. Here, all of the required timing differences for the system can be determined since each pair of detector elements can be coupled by a series of LORs (with four detector elements, there are six possible detector element combinations):

D10 is directly coupled to D30 by LOR 60
D20 is directly coupled to D40 by LOR 62
D30 is directly coupled to D40 by LOR 65
D10 is indirectly coupled to D40 (through D30) by LOR 60 and LOR 65
D10 is indirectly coupled to D20 (through D30 and D40) by LOR 60, LOR 65, and LOR 62
D20 is indirectly coupled to D30 (through D40) by LOR 62 and LOR 65

This example indicates that when there are more than two detectors, some degree of "one-to-many" coupling of elements is required in the measurements. In this case, the additional source provided one-to-many coupling of detectors D30 and D40.

FIG. 4 and FIG. 5 show two examples of one-to-many coupling within a group of detectors that allows determination of the required independent offset values within those groups along with an additional coupling. For example, in FIG. 5, the LORs 67 connecting the first group of detectors allows to calculate five independent offset correction values. Similarly, the LORs 69 connecting the second set of detectors allow to calculate an additional five independent offset values, bringing the total number of determined offset values to 10. This total of 10 is one short of the required 11 independent offset values. This shortfall has occurred because there is no cross-coupling between the two sets of LORs with the single limited-extent source 50. This example indicates that, although one-to-many coupling within a group or set allows for the determination of the relative offsets within that set, cross-coupling of sets is also necessary to fully calibrate the timing response of a system. The requirements for one-to-many coupling and cross-coupling between sets of detector elements has been handled in several ways in the conventional art, as will be discussed below.

Complete timing calibration requires one-to-many coupling of all the detector elements to be calibrated. Conventional calibration methods generally use external and/or internal sources.

Several of the methods using external sources are represented in FIGS. 6A-6D. All of these methods achieve the required one-to-many coupling, including the cross coupling across sets of detector elements. For example, detector elements in a set could be the individual scintillator elements in a scintillator array of a single detector module. In this case, cross coupling means that the external source methods described provide coupling across the gaps between modules—i.e. LORs from some scintillator elements are coupled to scintillators in more than one detector module on opposing side of the detector ring.

In the following, a "phantom" is a specially designed object that is placed in the field of view of a scanner for the purpose of scanner calibration or evaluating scanner performance. For PET, the phantom usually includes a positron-emitting source (such as Ge-68 or F-18 or Na-22), and often surrounding material to ensure that the emitted positrons are converted to back-to-back 511 keV photons within a short range through annihilation with electrons in the surrounding material. The phantom may be as simple as just a holder or mount for the radiation source. The phantom may also include materials that are intended to scatter emitted radiation, or partially absorb emitted radiation. As an example, cylinder phantoms are often used in PET. A fill-able cylinder phantom might consist of an acrylic cylinder with a central void and a closable port. When in use, the central void can be filled with a radioactive liquid, such as fluorodeoxyglucose (FDG; labelled with F-18) mixed with water. Alternatively, a sealed-source cylinder phantom may be used. In this case, a plastic cylindrical shell can be filled with a cured epoxy to which an isotope, such as Ge-68, has been added prior to curing. A cylinder phantom emits radiation, and the material of the cylinder also scatters and attenuates the radiation. Phantoms can also include moving parts, either for calibration purposes or to simulate organ motion, such as a beating heart or breathing motion.

FIG. 6A shows a method using a large cylindrical phantom 51. The phantom may be, for example, a cylinder that is approximately 20 cm in diameter and as long as the axial field-of-view of the scanner, and filled with an epoxy containing Ge-68. As indicated by the representative LORs 61, the LORs through the phantom couple each scintillator element in the scintillator blocks 102 to many other scintillator elements, including scintillator elements in several different detector modules 101. The drawbacks of the method shown in FIG. 6A are that the phantom itself might weigh 20 kg, making it difficult to handle, and the phantom requires very heavy shielding (for example, approximately 150 kg of lead) to protect staff and patients when the phantom is not in use.

FIG. 6B shows a method using a moving phantom 52. In this case, the phantom may comprise a rod source of annihilation radiation (for example, Ge-68 in a steel sleeve) and a mechanism providing movement in a circular orbit within the field-of-view of the scanner. As the radiation source rotates, the representative LORs 61 couple each scintillator element in the scintillator blocks 102 to many other scintillator elements, including scintillator elements in several different detector modules 101. The complexity, cost, and maintenance of the mechanism which provides the movement of the source are drawbacks of this method.

FIG. 6C shows a method which uses a phantom comprising a cylindrical annihilation target 53 and a separate source of positrons (such as Ge-68; not shown in figure) that is relatively unshielded, so that positrons escape the source and annihilate with electrons in the annihilation target 53 to produce back-to-back 511 keV annihilation radiation. The annihilation target may be, for example, a plastic cylindrical shell that is approximately 20 cm in diameter and as long as the axial field-of-view of the scanner. As with the methods above, the LORs through the phantom, as represented by 61, couple each scintillator element in the scintillator blocks 102 to many other scintillator elements, including scintillator elements in several different detector modules 101. The large size of the annihilation target is a drawback to this method because it can be difficult to handle. The large size can also make storage, when not in use, inconvenient.

Finally, FIG. 6D shows a method in which the one-to-many coupling is provided by surrounding source of annihilation radiation with a substantial mass of scattering media. In this case the phantom 54 may comprise a Ge-68 rod source surrounded by a steel cylinder that is approximately 10 cm from inner diameter to outer diameter. This method has several drawbacks. First, the phantom is rather heavy, and can be difficult to handle. Second, due to attenuation and the low efficiency for scatter of 511 keV gamma rays, very few of the gamma rays that are emitted from the source are actually available to provide one-to-many coupling, so the data acquisition can be long and the convergence of iterative methods for estimating the offsets can be slow. Additionally, the uncertainty in the scatter location reduces the accuracy, particularly for the timing resolution (~200 ps) that is achievable in state-of-the-art systems.

Conventional methods using internal sources are represented in FIGS. 7A-7B.

FIG. 7A illustrates a method which uses internal radiation to couple each element in the scintillator block 102 to many elements around the detector ring, as indicated by the representative LORs 61. Hours of data acquisition are generally required to reach sufficient accuracy. Also, since the internal radiation from Lu-176 produces a very broad energy spectrum, the energy range of accepted events is limited to two fairly narrow windows (one around 511 keV and the other around 307 keV, where one of the strong emissions of Lu-176 is present. The result of the application of these energy windows is an extreme reduction in the available counts.

This effect is illustrated in FIG. 16. The data shown in this figure were acquired on a PET system using scintillator crystals containing Lu-176. The full Lu-176 coincident energy spectrum is indicated by 900. In the full spectrum 900 there were 78,416,224 counts. The coincident energy spectrum after applying the two energy windows is indicated by 950. The amplitude of spectrum 950 is severely reduced because of the relatively low joint probability that one event of the coincident pair is in the 511 keV window (435-625 keV, in this case) while the other event is in the 307 keV window (250-350 keV, in this case). In the energy-windowed spectrum 950 there are 10,241,786 counts. Thus, the application of the two energy windows has helped to limit the effect of walk on the measured timing offset, but it has also reduced the available counts to approximately 13% of the counts in the full spectrum 900.

FIG. 7B shows an alternative method using internal radiation. In this method, only LORs connecting adjacent scintillator blocks 102 are used, as indicated by representative LORs 61. In addition to suffering from long data acquisition times, limiting the LORs to adjacent modules has another severe drawback. All scintillator elements must be connected by LORs to scintillator elements in adjacent blocks, but the penetration depth of the emitted internal radiation (mainly 202 keV and 307 keV gamma rays; much lower energy than the 511 keV gamma rays detected in PET) is limited. Therefore, the method is limited to calibration of blocks which are generally less than ~20 mm across.

SUMMARY

To summarize, the drawbacks of the conventional TOF PET art can generally be described in two ways. For methods using external radiation sources, either the phantoms are large and difficult to handle or they require complex mechanical motion. On the other hand, methods using internal radiation are generally very slow.

The embodiments presented herein make use of a combination of a single stationary "limited extent" external source and internal radiation in a novel way which has significant advantages. The calibration method divides the timing calibration into two steps. In the first step, the single stationary, limited-extent external source, is used to obtain "relative timing offset" within groups of processing units. In the second step, "internal radiation" is used to obtain offsets between groups of processing units. The total offset is then the sum of the "relative timing offset" and the "processing unit offset".

Using a single stationary limited-extent external source eliminates the major drawbacks of the external source methods in the conventional TOF PET methods. Furthermore, dividing the process into two steps allows to significantly reduce the total amount of data required for the internal radiation process, thereby eliminating the major drawback of the internal radiation methods in the conventional TOF PET.

The number of counts required for the internal radiation step is significantly reduced for two reasons. First, by determining a relative offset in the external source step, the offsets determined in the internal radiation step are only "processing unit offset". This means that all of the counts from all of the scintillator crystals in a processing unit can be aggregated, thereby reducing the acquisition time. As an example, if the scintillator array in one processing unit has 10×10=100 crystals, then the number of counts required to achieve the desired accuracy at the processing unit level is reduced by a factor of 100 compared to the number of counts to achieve the same accuracy in the external source step at the crystal level. In addition, by pre-correcting the internal radiation timing data using the results from the external source step, the width of the distributions in the internal radiation data are significantly reduced. This effect is even larger when the relative offset correction obtained in the external source step includes walk correction, and, in particular, non-linear walk correction.

The offset values discussed above relate to variation in delay in various components in the detector system. One source of such variation can be an energy-dependence in the timing discriminator which produces the timing signal. FIG. 11 illustrates the leading-edge discriminator which is often used in TOF PET systems. A time, t, is assigned when the signal level crosses a threshold value. FIG. 11 shows an example of the signals that might be produced by three different energy gamma rays interacting with a detector element at the same time. The three different signals correspond to energies $E_1$, $E_2$, and $E_3$ (with E1>E2>E3). Even though the three gamma rays arrive at the same time, the times ($t_1$, $t_2$, and $t_3$, respectively) at which they cross the threshold value are different. This effect is often referred to as timing walk.

Correcting for walk before the 'internal radiation' step also allows us to use all of the counts acquired, rather than limiting the analysis to events in narrow energy windows (as was done in the prior-art), as shown in FIG. 16. This further reduces the required acquisition time.

FIG. 8A shows an internal radiation timing distribution before applying the relative offset correction obtained from the external source, and FIG. 8B shows the distribution for the same data after applying the timing corrections from the first step (including non-linear walk correction). In this case, the widths of the timing distributions are reduced by a factor of more than 2. To achieve the same statistical uncertainty in the processing unit offset, the effect of this reduction in distribution width is roughly equivalent to increasing the number of counts by more than a factor of 4. Therefore, by separating the process into two steps, and pre-correcting the data in the second step before performing the calculations, the amount of data required (or the acquisition time) for the internal radiation step has been reduced by approximately a factor of 100×4=400, in the example provided (compared to the case of using internal radiation at the crystal level and without first pre-correcting the data). This takes the acquisition time from several hours in the case of using internal radiation for the entire calibration to on the order of a minute for the method described here, and this was done without the use of large or moving external sources.

Timing offset calibration requires that all processing units to be calibrated are coupled together by coincident events. One processing unit could be one element at any stage of the electronics architectures in FIG. 9 and FIG. 10. The processing units to be calibrated could be coupled by coincident events directly. The processing units to be calibrated could also be coupled by coincident events indirectly. For example, if processing unit 1 is coupled to unit 2, and unit 2 is coupled to unit 3, then unit 1 and unit 3 are indirectly coupled.

A small, lightweight limited-extent external source (such as a small-but-finite-diameter line source) can be used for calibrating relative crystal offset within processing units and walk (without source movement or multiple sources).

Internal radiation (even at a low activity level) can be used to measure processing unit offset (after correcting for relative crystal offset and walk). Pre-correcting for relative crystal offset and walk narrows initial timing distributions, resulting in reduction in required number of counts to achieve specific processing unit offset accuracy, making acquisition time for internal radiation reasonable. Also, walk correction also allows use of all events from internal radiation, rather than being limited to a small range of energies near 511 keV, for example.

Total offset is then the sum of relative crystal offset and processing unit offset.

Advantages include reducing the need for large limited extent source, source movement, or multiple sources. Small limited-extent source is easier to handle and shield, and less costly to replace. Furthermore, processing unit offset can be re-calibrated periodically using only internal radiation.

During initial full timing calibration, timing offset and timing walk within opposite processing unit pairs are calibrated by placing am annihilation radiation, e.g. a positron emitting line source at the scanner center. The line source should be thick enough that each row of crystals are coupled to more than one row of crystals in the opposite processing unit. After correcting for relative timing offset and timing walk within opposite processing unit pairs, timing offset between processing units is calibrated using internal radiation in the crystal.

Here, internal radiation is radiation which results from decay of radioactive material that is part of the scintillator array (in the crystal, on the crystal surface, in the reflector material, etc.). A typical internal radiation is background radiation from naturally occurring isotopes of the scintillator material. Lu-176 in LYSO is an example of background radiation. Internal radiation could also be purposely added or doped into the scintillator material. Co-60 is another example of a material which could be added to the scintillator material.

Requirements for internal radiation include the following: the decay process includes at least two (nearly) simultaneous emissions (for example, beta followed immediately by gamma), from which coincidence events could be formed; or the decay process includes one emission, from which coincidence events could be formed from Compton scatter in detectors caused by this emission; the half-life is greater than 10 years, so there is significant self-activity over the life of the scanner; activity is in the range of 100 to 1000 Bq per $cm^3$, so data acquisition time is practical and not too many random events are formed; energies of emission is a few hundred keV to ~1 MeV; and candidates include Lu-176 and Co-60.

During daily clinical use, timing offset correction and timing walk correction from previous timing calibration is applied before re-calibrating the timing offset at the processing unit level. The timing offset per processing unit could be calculated using internal radiation and an annihilation radiation, e.g. a positron emitting line source at center together, or the timing offset per processing unit could be calibrated using internal radiation while scanner is not in use. One processing unit could be one element at any stage of the electronics architectures in FIG. 9 and FIG. 10.

BRIEF DESCRIPTION OF THE DRAWINGS

The application will be better understood in light of the description which is given in a non-limiting manner, accompanied by the attached drawings in which:

FIGS. 6A-6D show schematics of various embodiments of external positron sources within the detector ring.)

FIG. 8A shows an internal radiation timing distribution before applying the relative offset correction obtained from the external source.

FIG. 8B shows the distribution for the same data after applying the timing corrections (including non-linear walk correction).

FIG. 11 shows the leading-edge discriminator used in TOF PET systems.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

Figure 1:
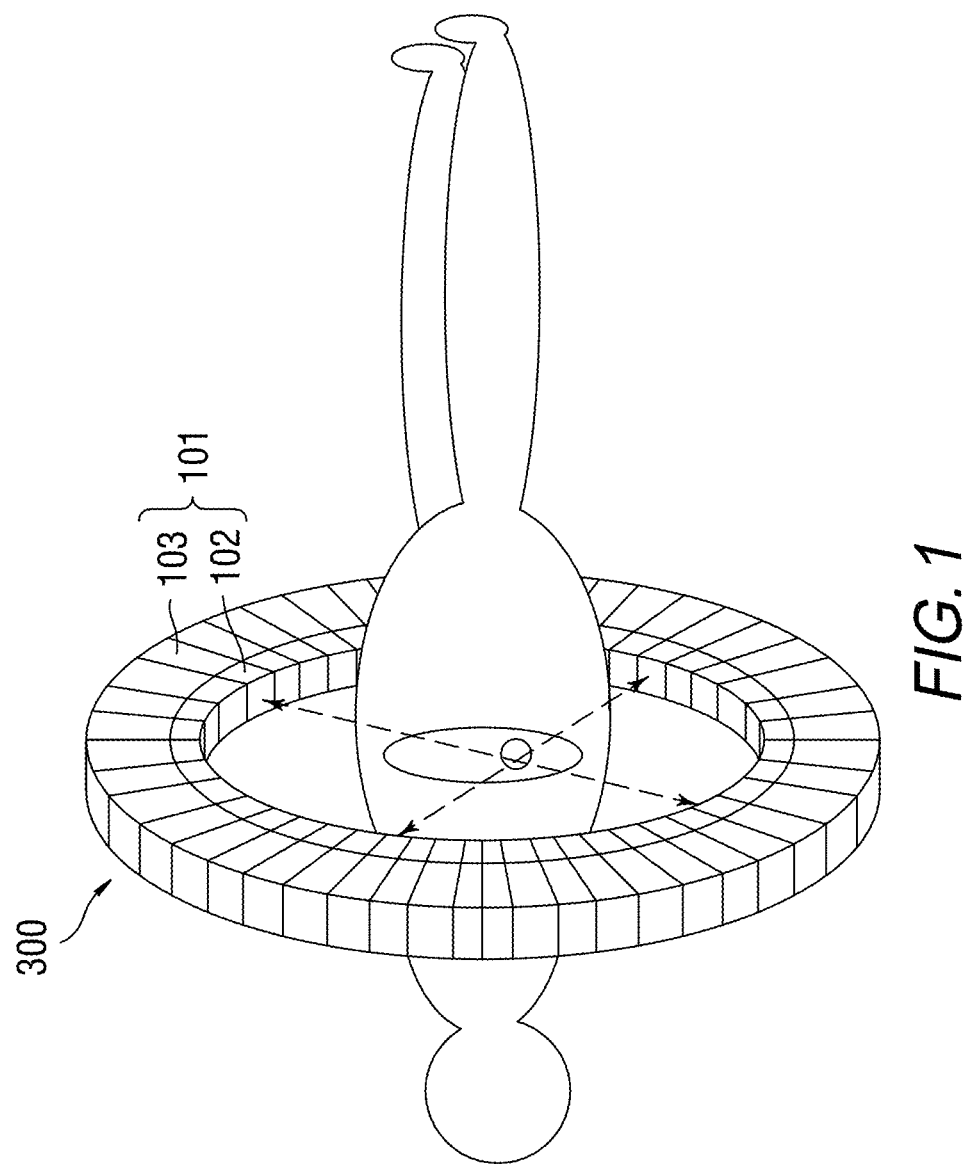
FIG. 1 shows a schematic of a PET scanner.
Figure 2A:
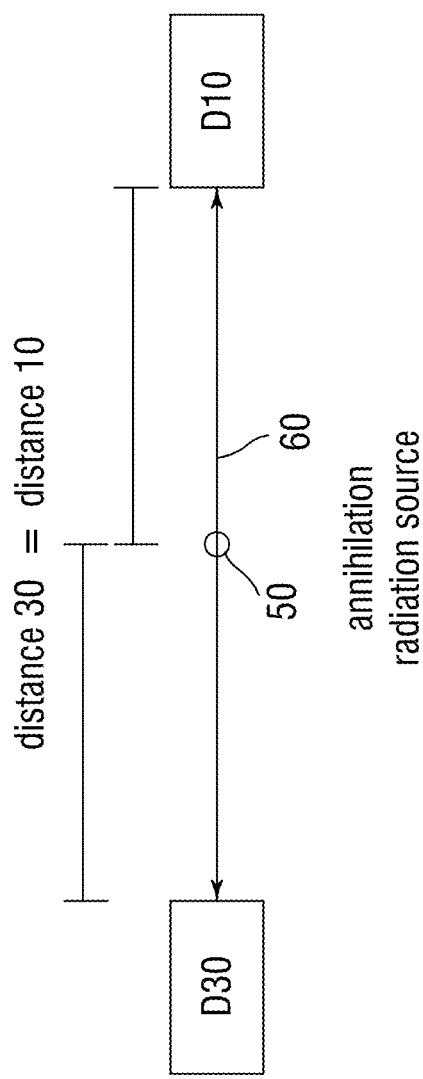
FIG. 2A shows a schematic of an example position of an external source relative to opposite detectors.
Figure 2B:
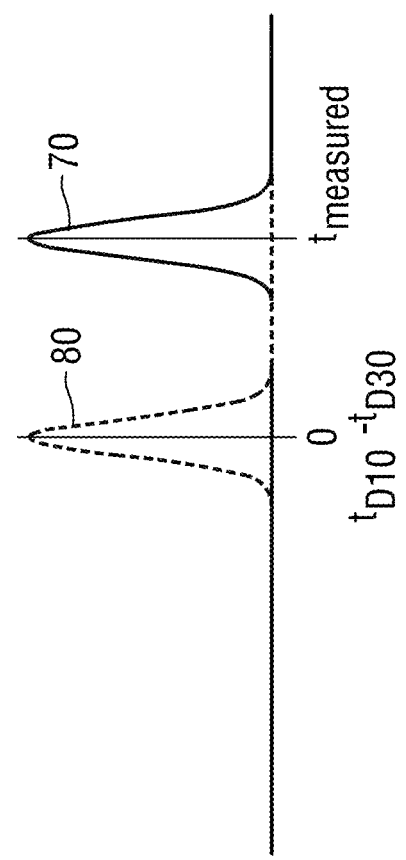
FIG. 2B shows a TOF difference histogram between the two detectors of FIG. 2A.
Figure 3:
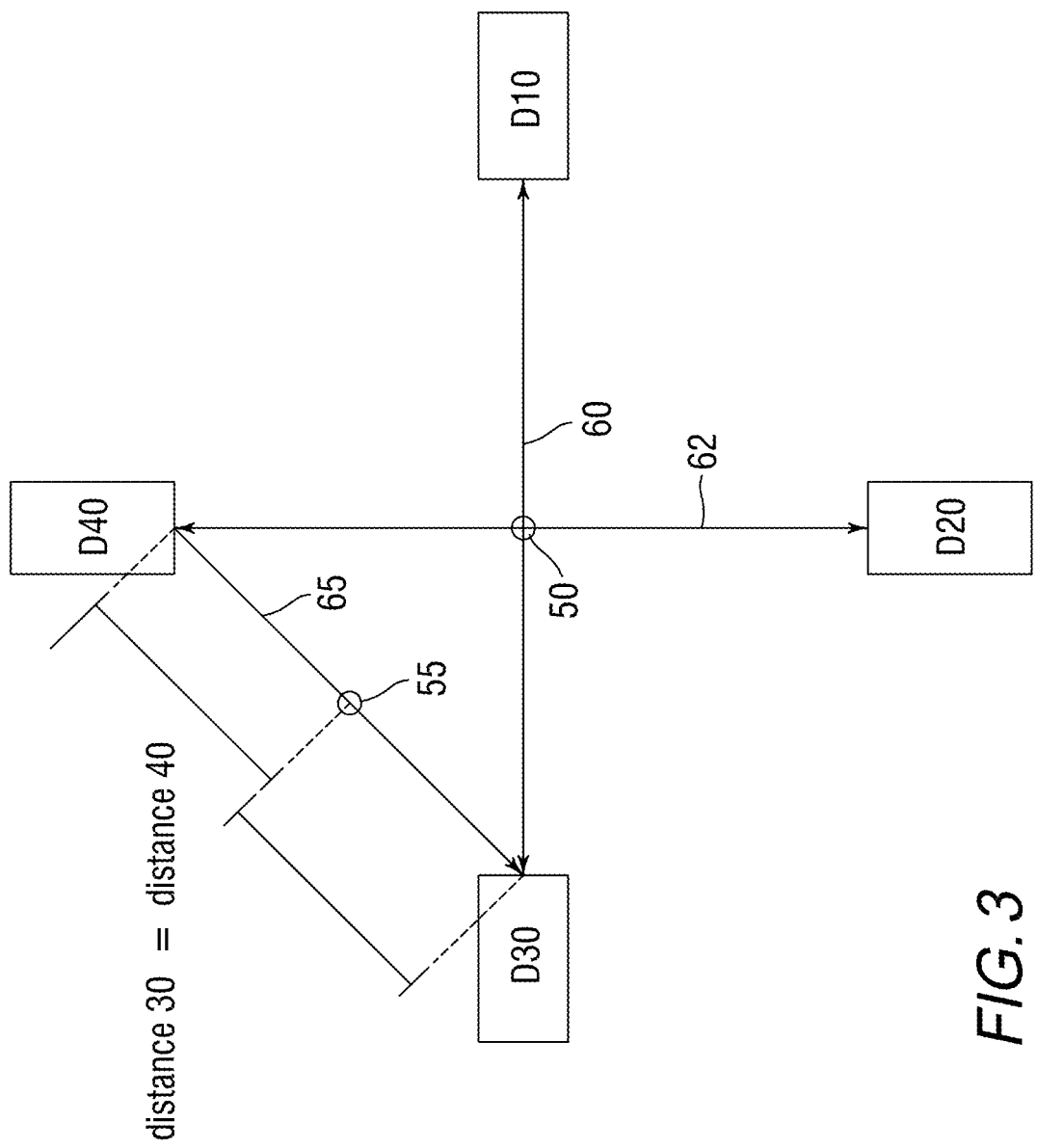
FIG. 3 shows a schematic of another example position of a pair of external sources relative to opposite detectors.
Figure 4:
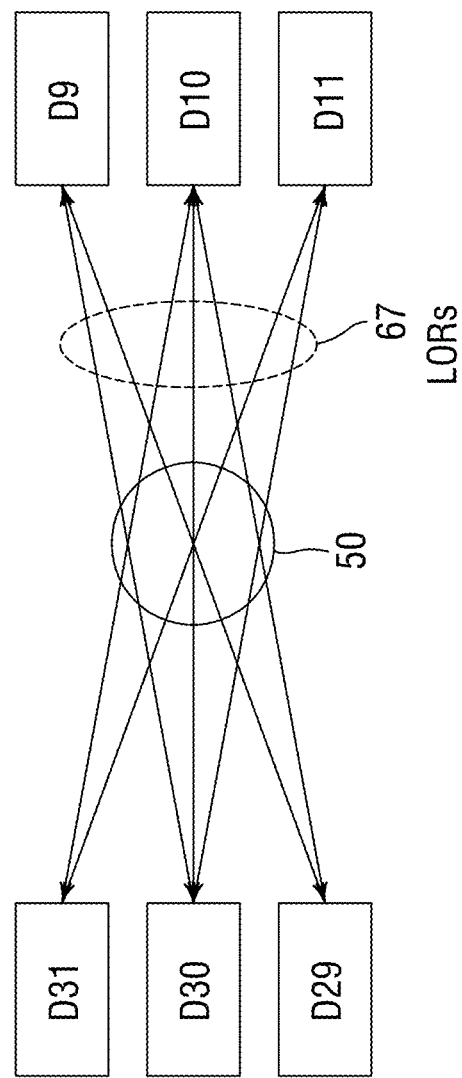
FIG. 4 shows a schematic of another example position of an external source relative to opposite detectors.
Figure 5:
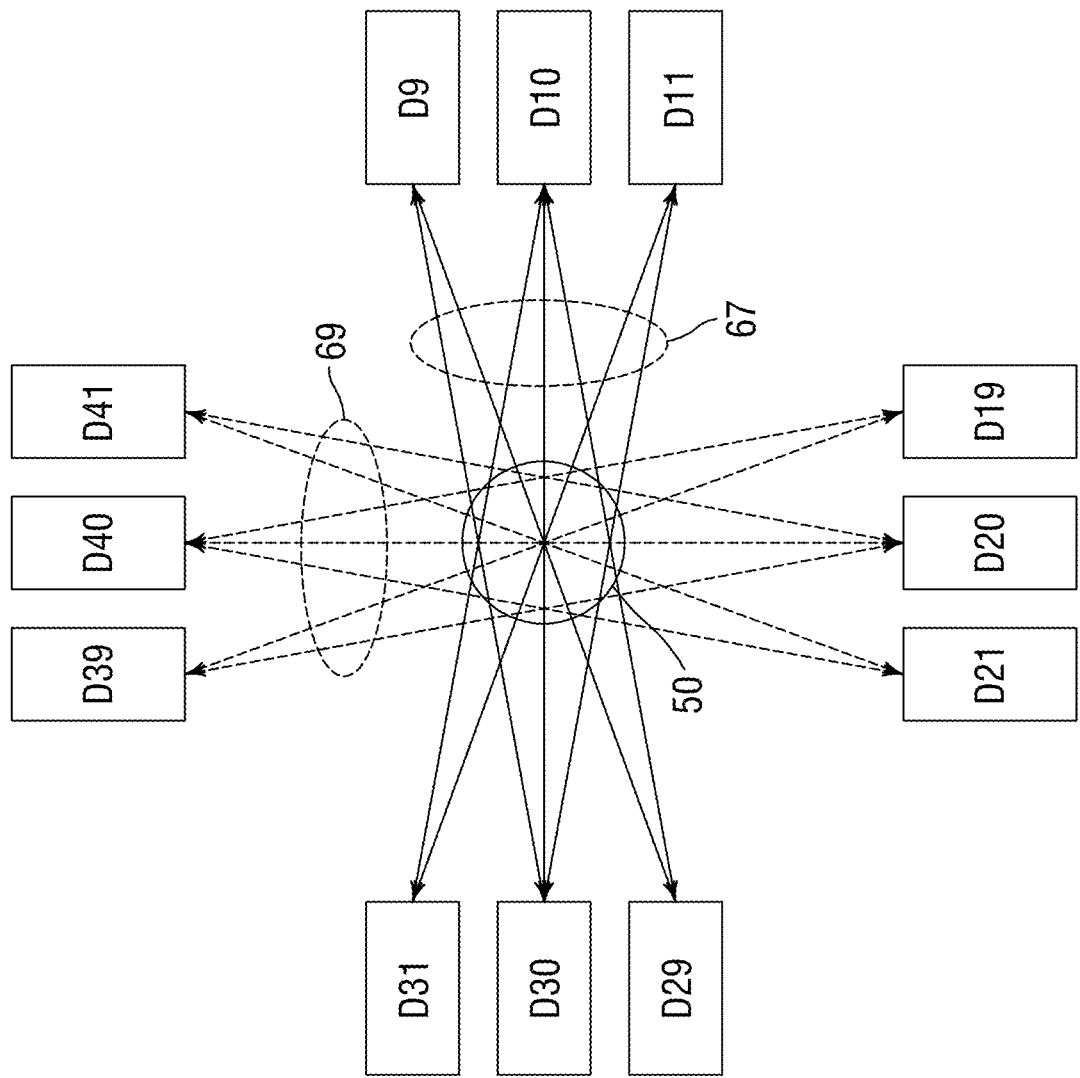
FIG. 5 shows a schematic of another example position of an external source relative to opposite detectors.
Figure 7B:
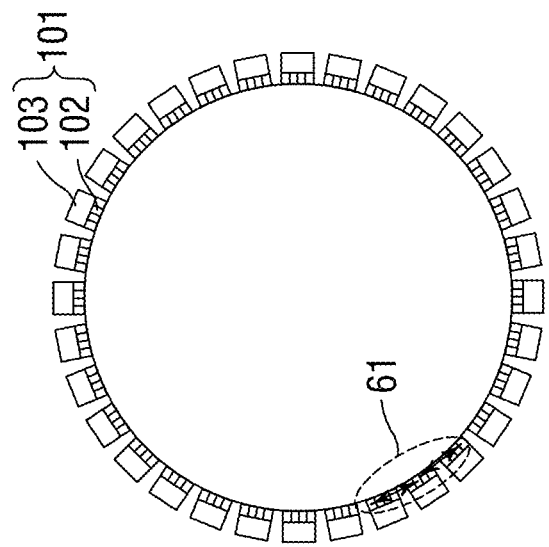
FIGS. 7A-7B show schematics of various embodiments of internal sources within the detector ring.
Figure 7A:
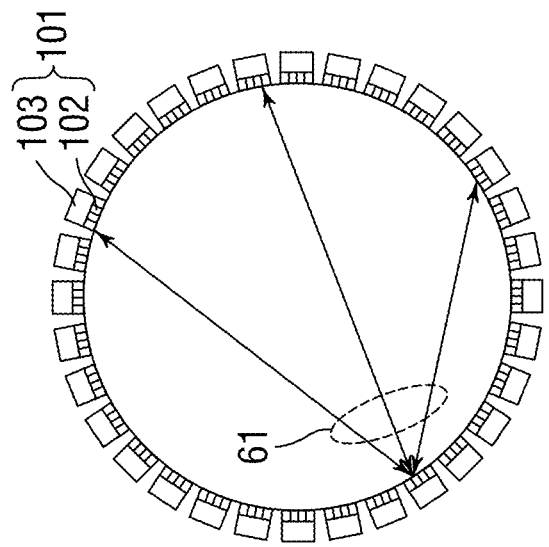
Figure 9:
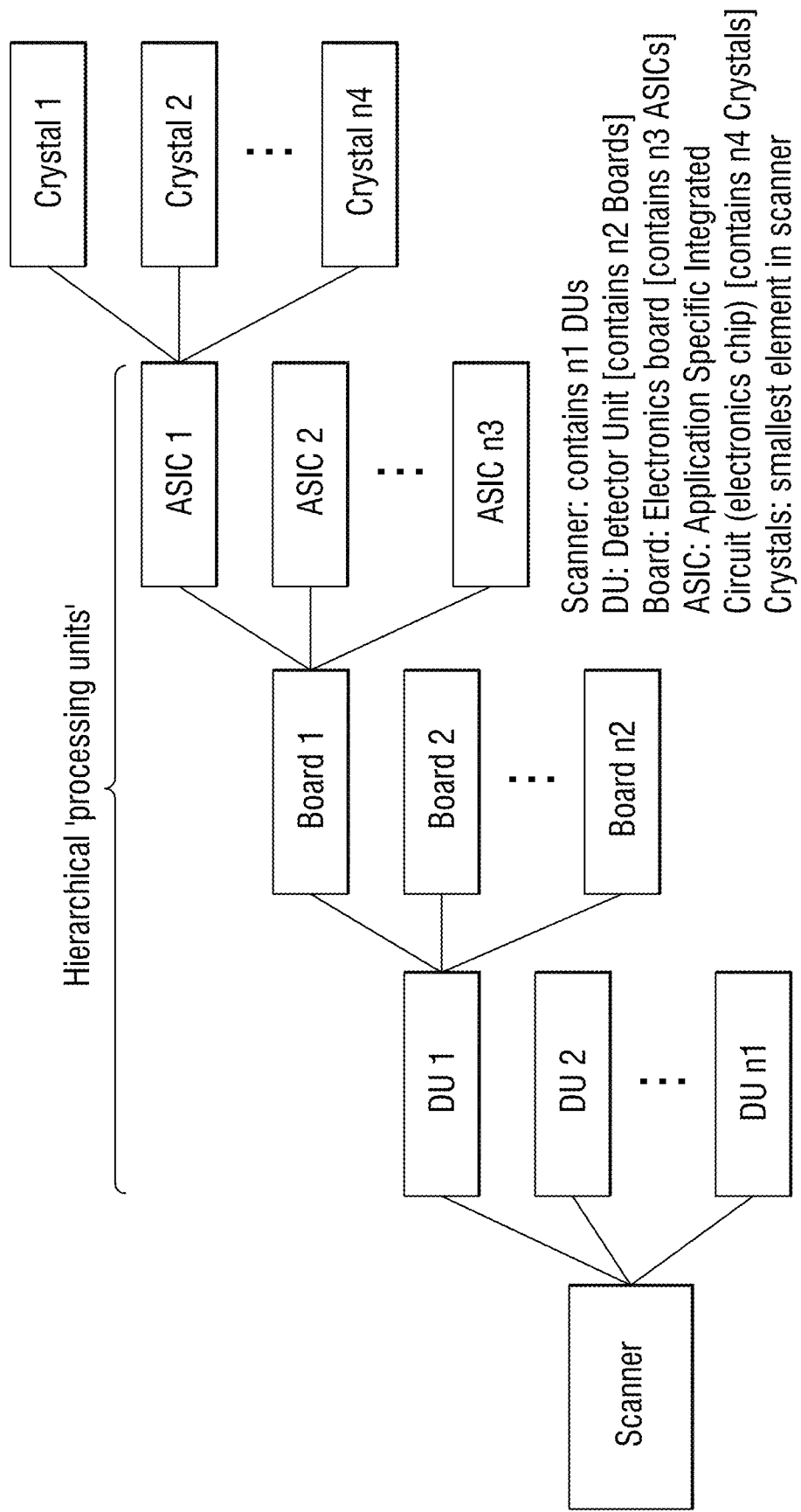
FIG. 9 shows a schematic of an example layout of different stages of timing calibration.
Figure 10:
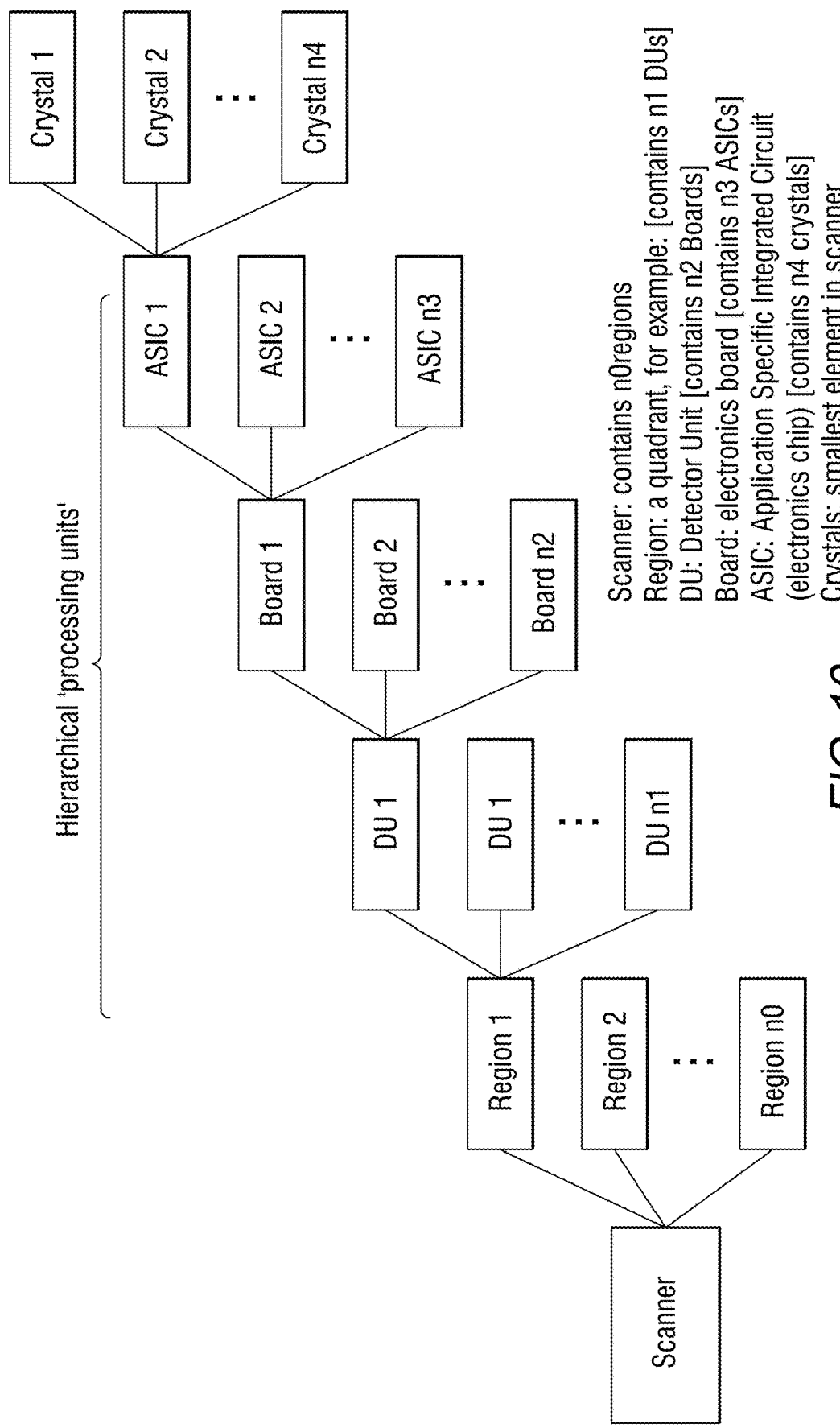
FIG. 10 shows a schematic of another example layout of different stages of timing calibration.

A PET scanner in the present embodiments may have different electronics architectures. Non-limiting example layouts are shown in FIG. 9 and FIG. 10, where:

PET scanner: a whole scanner, usually in the form of a ring.

Region: a relatively large part of the scanner, such as a quadrant, which consists of advanced data processing, data transfer, clock control, signal processing, etc. A scanner might have several regions. Timing offset/drift due to clock distribution could be on a region basis.

Detector unit (DU): a relatively isolated module, which consists of data transfer, clock control, signal processing, etc. A region might have 10-20 DUs. Timing offset/drift due to clock distribution could be on a DU basis.

Board: an electronics board, which consists of signal processing circuitry for a number of channels. A DU might have 5-20 boards. Timing offset/drift due to power supply could be on a board basis.

ASIC: the smallest signal processing unit, which usually consists of one timing processing channel and several energy processing channels. A board might have 1-10 application specific integrated circuits (ASICs). Timing offset/drift could be on an ASIC basis.

Crystal: the smallest element in the scanner. An ASIC might perform signal processing for several tens of crystals.

Timing calibration is usually done at different stages. The number of elements at each stage of the electronics architecture is scaled by approximately an order-of-magnitude. For the same statistical uncertainty, the acquisition time and analysis time for calibrating the timing offset at each stage varies significantly. For example, a DU might contain 500 to 1000 crystals, so calibrating the DU offset requires approximately $\sqrt{(500 \text{ to } 1000)}$ or 20-30 times shorter acquisition time than calibrating the crystal offset (and this ignores computation time).

However, timing calibration might only need to be done at certain stages. After initial timing calibration, timing drift could happen at certain stages depending on the cause of the timing drift. Then, maintenance timing calibration only needs to be performed for stages where timing drift occurs, so it could be made much faster.

Timing walk can be corrected by including an energy-dependent term in the offset correction. Correcting the timing walk results in better timing resolution (i.e. a narrower distribution of measured timing differences). Typically in PET, imaging is performed only using detected gamma rays in a narrow window around 511 keV. When only events in a narrow energy window are used, a linear walk correction (i.e. a walk-correction that only depends linearly on the energy) is usually sufficient. For example, an offset including a linear walk correction can be written as $$t_{offset} = t_{offset}(E=511) + W_1(E-511)$$

where $W_1$ is the linear walk-correction coefficient. The walk-correction can be expanded to include non-linear terms, such as $$t_{offset} = t_{offset}(E=511) + W_1(E-511) + W_2(E-511) + \ldots + W_n(E-511)^n$$

where $W_1$ through $W_n$ are walk correction coefficients.

Here, since the method presented herein uses events across a very wide energy range for the "internal radiation" portion of the calibration (to reduce the total acquisition time to a practical range), a non-linear walk correction provides substantial improvement in performance. Since any function that would be used for walk correction can be represented by a Taylor series expansion, this is equivalent to toffset=f(E) where f is a function, which may be non-linear.

During initial full timing calibration, the timing offset per crystal and timing walk per crystal are calibrated. The line source should be thick enough that each row of crystals is coupled to more than one row of crystals in the opposite DU. Data with positron-emitting line source and internal radiation could be acquired separately or simultaneously.

In one embodiment, data with positron-emitting line source and internal radiation could be acquired separately. The positron-emitting source may be at least one of a Ge-68 line source, a F18-FDG line source or a Na-22 line source.

In particular, during data acquisition with positron-emitting line source, the disclosed method: places the positron-emitting line source at the center of the scanner field of view (FOV); and acquires coincidence data with the positron-emitting line source. Standard clinical data acquisition FOV and coincidence timing window could be used. The number of coincidence events with positron-emitting line source needs to be enough to calibrate the peak position from the TOF difference histogram for each of the crystals.

During data acquisition with internal radiation, the disclosed method: removes all radiation source from the scanner; and acquires coincidence data with internal radiation. Standard clinical data acquisition FOV could be used. The coincidence timing window should be large enough to allow radiation particles, such as gamma particles, to travel across the scanner. The number of coincidence events with internal radiation needs to be enough to calibrate the peak position from the TOF difference histogram for each of the DUs.

In still another embodiment, data with positron-emitting line source and internal radiation could be acquired simultaneously.

In particular, the disclosed method: acquires coincidence data with positron-emitting line source and internal radiation. Standard clinical data acquisition FOV could be used. The coincidence timing window should be large enough to allow radiation particles to travel across the scanner. The number of coincidence events with positron-emitting line source needs to be enough to calibrate the peak position from the TOF difference histogram for each of the crystals, and the number of coincidence events with internal radiation needs to be enough to calibrate the peak position from the TOF difference histogram for each of the DUs.

During the data analysis, if data with positron-emitting line source events and internal radiation events are acquired simultaneously, they could be separated from TOF difference. FOV can also be used to separate line source events from internal radiation events, as line source events concentrate in narrow FOV while internal radiation events have a broader coverage.

During the data analysis, timing correction is split to three different parts: non-energy-dependent relative timing offset per crystal within opposite DU pairs, timing walk correction coefficient per crystal, and non-energy-dependent timing offset between DUs. Non-energy-dependent relative timing offset per crystal within opposite DU pairs and timing walk correction coefficient per crystal are calculated from positron-emitting line source data, whereas non-energy-dependent timing offset between DUs are calculated from internal radiation data. In the description below, relative timing offset within opposite DU pairs and timing offset between DUs refer to non-energy-dependent terms.

With regard to timing calibration within opposite DU pairs, the method splits coincidence data with positron-emitting line source to N/2 DU pairs, for a PET scanner with N DUs. The relative timing offset within opposite DU pairs and timing walk correction coefficients could be calibrated in parallel for different DU pairs. If the line source is not perfectly centered, the annihilation position correction is applied to the TOF difference of all the events. The relative timing offset per crystal within opposite DU pairs could be calculated iteratively, by: i) calculating the timing offset by finding the peak position of the timing histogram for each crystal ii) correcting the TOF difference for the timing offset per crystal calibrated above, then repeating step i) and step ii) until the sequence converges iii) the final timing offset per crystal within a DU pair is the sum over the timing offset per crystal calibrated in all iterations.

After correcting for relative timing offset per crystal within opposite DU pairs, the timing walk correction coefficient per crystal could be calculated as the following: i) for each specific crystal, plotting the timing vs energy curve, the LORs connecting this specific crystal and any crystals on the other side are considered and ii) calculating the walk correction coefficient per crystal by applying appropriate fit (e.g., linear fit or exponential fit) to the timing-energy curve for that crystal.

With regard to timing offset calibration between DUs, the method applies timing offset within DU pair correction and timing walk correction to the radiation coincidence data. Event position correction to the TOF difference is not necessary due to symmetry in DU pair TOF difference histograms. However, event position correction could also be applied to the TOF difference of all the events to achieve narrower timing histograms. The timing offset per DU could be calculated iteratively by: i) calculating the timing offset by finding the peak position of the timing histogram for each DU ii) correcting the TOF difference for the timing offset per DU calibrated above, then repeating step i) and step ii) until the sequence converges iii) the final timing offset per DU is the sum over the timing offset per DU calibrated in all iterations.

In another embodiment, the timing offset per DU may also be calculated analytically. In particular, the TOF difference histogram for each DU pair covered by data acquisition FOV is calculated. The timing center for each DU pair is calculated by finding the peak position of the TOF difference histogram. A set of equations could be formed from the timing center per DU pair. The variables are the timing offset per DU. The rank of the coefficient matrix in the equations should be equal to the number of DUs. The timing offset per DU could be calculated by solving the above equations. The timing offset per DU could also be calculated using Neutral Network from timing center per DU pair.

In still another embodiment, the timing offset per DU may also be calculated using Neural Networks. In particular, the input to the Neural Network could be an array where (for example) each column represents the timing histogram for a single DU. The output would be the offset for each DU. The Neural Network could be trained using target offset data that is generated by using any conventional timing offset calibration method. Training would require data from a large number of systems. Since only a few systems will have been built when the network must be trained, data augmentation (described below) may be used to generate a large number of additional training data sets.

In particular, the data augmentation: acquires data from any existing systems (for example, 3 to 4); calibrates each system using conventional timing offset calibration; uses the calibration to generate corrected timing histograms for each DU pair; for many system realizations (hundreds or thousands), generates random timing offsets for each DU, and applies the random timing offsets to the corrected timing histograms to build augmented data sets for DU in each of the system realizations. For these augmented data sets, the target offset is known from the random timing offsets that we generated for each DU.

The neural network design could be a convolutional Neural Network (to reduce the number of parameters required). In this case, the convolutional layers would be one-dimensional-only acting on the histogram from a single DU (such as the columns of the input matrix, if, as described above, each column represents the histogram from a single DU).

The disclosed method may perform quick timing calibration with internal radiation.

In particular, timing offset per processing unit is calculated. The processing unit here could be a DU, or it could also be an electronics processing unit within a DU. The data acquisition-with internal radiation removes all radiation sources from the scanner and acquires coincidence data with internal radiation. Standard clinical data acquisition FOV could be used. The coincidence timing window should be large enough to allow radiation particles to travel across the scanner. The number of coincidence events with internal radiation needs to be enough to calibrate the peak position from the TOF histogram for each of the processing units.

In the data analysis, timing offset correction and timing walk correction from initial timing calibration is applied before performing quick timing calibration. The data analysis procedure to calibrate timing offset per processing unit in quick timing calibration is the same as the data analysis procedure to calibrate timing offset per DU in initial full timing calibration.

In another embodiment, the disclosed method may perform quick timing calibration with internal radiation and positron-emitting line source. If timing offset for processing units smaller than DUs needs calibration, quick timing calibration could also be calculated similarly as initial timing calibration.

The data acquisition is the same as the initial timing calibration, except that: the number of coincidence events with positron-emitting line source needs to be enough to calibrate the peak position from the TOF difference histogram for each of the processing units, and the number of coincidence events with internal radiation needs to be enough to calibrate the peak position from the TOF histogram for each of the processing units.

Data analysis is similar as initial timing calibration.

Timing offset correction and timing walk correction from initial timing calibration is applied before performing quick timing calibration. Timing offset per processing unit within opposite DU pairs is calculated using positron-emission line source at center data, similarly as in initial full timing calibration. Timing offset between DUs is calibrated using internal radiation, the same as in initial full timing calibration.

Figures 12A, 12B:
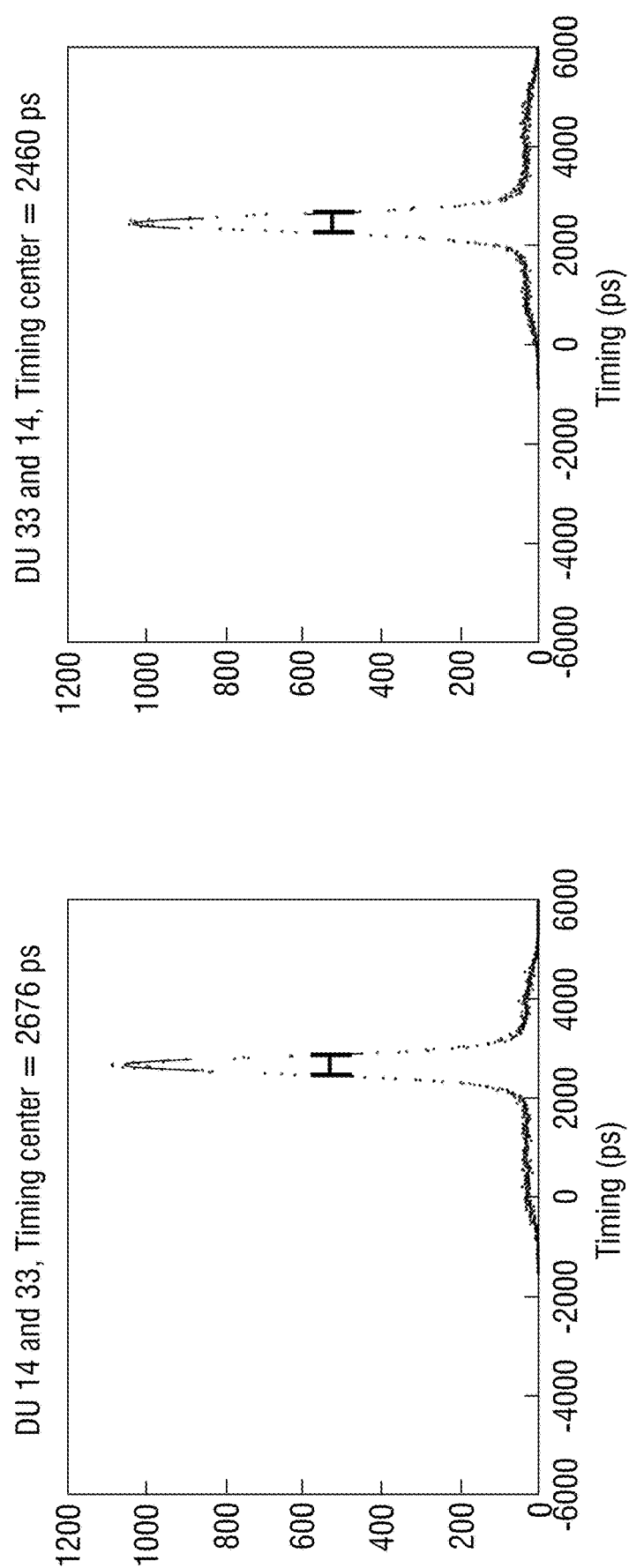
FIGS. 12A and 12B show a TOF difference histogram between DU 14 and DU 33 from Lutetium background radiation data. Timing center is found by applying parabola fitting to the peak region.

FIG. 12A and FIG. 12B show example DU pair TOF difference histograms from lutetium background radiation data when calculating timing offset between DUs. TOF difference is calculated as (time stamp for the first hit–time stamp for the second hit).

The timing center of the DU pair TOF difference histograms could be found from Gaussian fitting to the whole curve or parabola fitting to the peak region. Timing center of the DU pair TOF difference histograms could also be found using Neutral Network (NN).

Equations for determining the timing offset per DU are as the following.

$$T\text{center}_{14\text{-}33} = T\text{offset}_{14} - T\text{offset}_{33} - T\text{diff}_{distance}$$

$$T\text{center}_{33\text{-}14} = T\text{offset}_{33} - T\text{offset}_{14} - T\text{diff}_{distance}$$

$$T\text{offset}_{14} - T\text{offset}_{33} = (T\text{center}_{14\text{-}33} - T\text{center}_{33\text{-}14})/2$$

$T\text{diff}_{distance}$ is event position correction to the TOF difference, which is cancelled out when calculating timing offset difference between DU 14 and DU 33.

Figure 13:
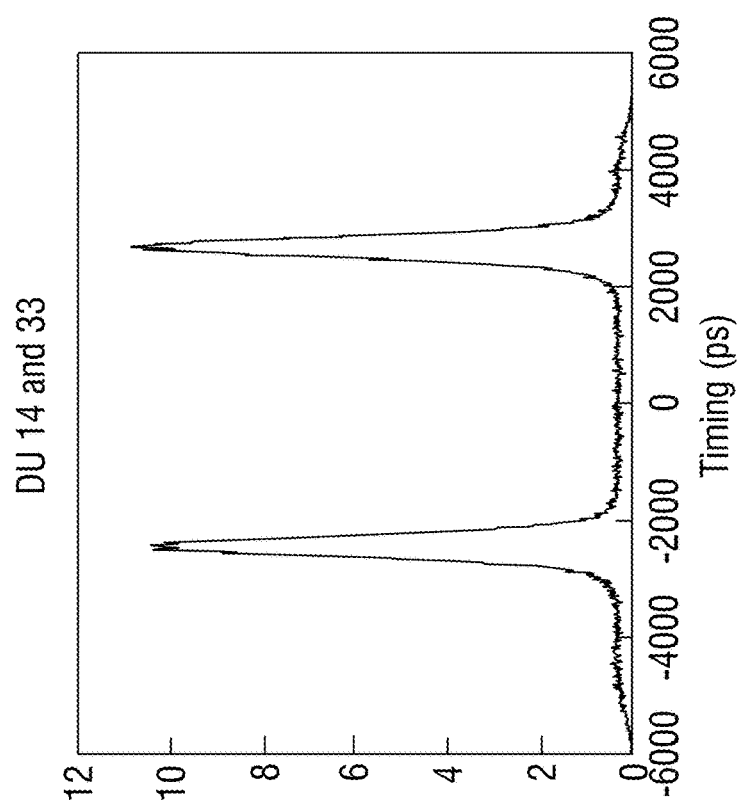
FIG. 13 shows a TOF difference histogram between DU 14 and DU 33 from Lutetium background radiation data.

FIG. 13 shows another way of calculating DU pair TOF difference histograms from lutetium background radiation data when calculating timing offset between DUs. TOF difference is calculated as (time stamp for DU 14–time stamp for DU 33). Timing center of the DU pair TOF difference histograms could be found from Gaussian fitting to the whole curve or parabola fitting to the peak region. Timing center of the DU pair TOF difference histograms could also be found using Neutral Network (NN).

Equations for timing offset per DU is as the following.

$$T\text{center}_{left} = T\text{offset}_{14} - T\text{offset}_{33} - T\text{diff}_{distance}$$

$$T\text{center}_{right} = T\text{offset}_{14} - T\text{offset}_{33} + T\text{diff}_{distance}$$

$$T\text{offset}_{14} - T\text{offset}_{33} = (T\text{center}_{right} + T\text{center}_{left})2$$

Figure 14:
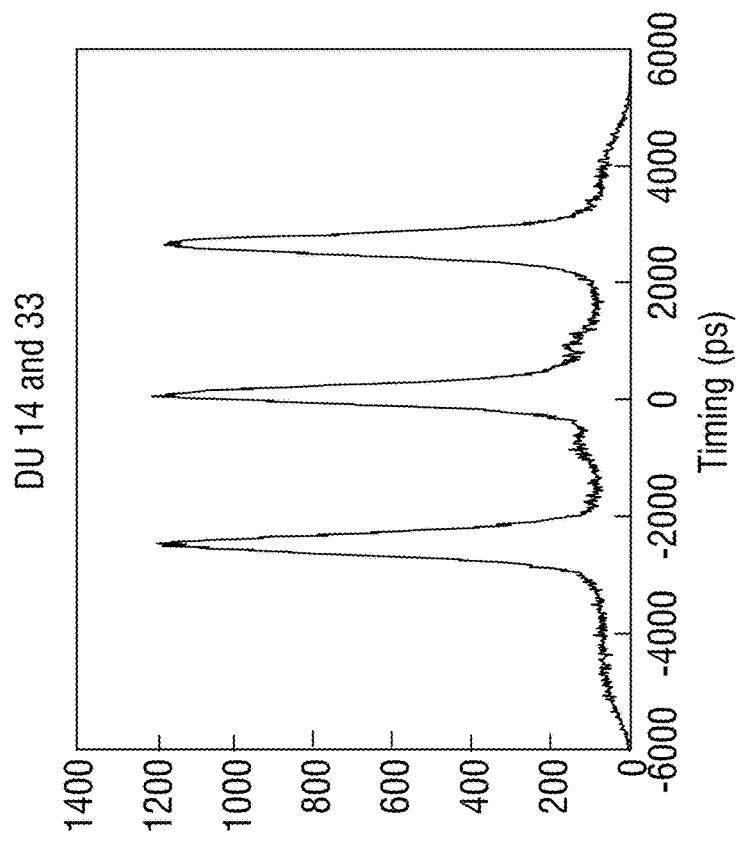
FIG. 14 shows a TOF difference histogram between DU 14 and DU 33 from Ge line source and background radiation data.

FIG. 14 shows example DU pair TOF difference histograms from lutetium background radiation data and Ge line source data acquired simultaneously. TOF difference is calculated as (time stamp for DU 14–time stamp for DU 33). The positron-emitting line source data and the lutetium internal radiation data could be separated from time of flight (TOF) difference.

Figure 15B:
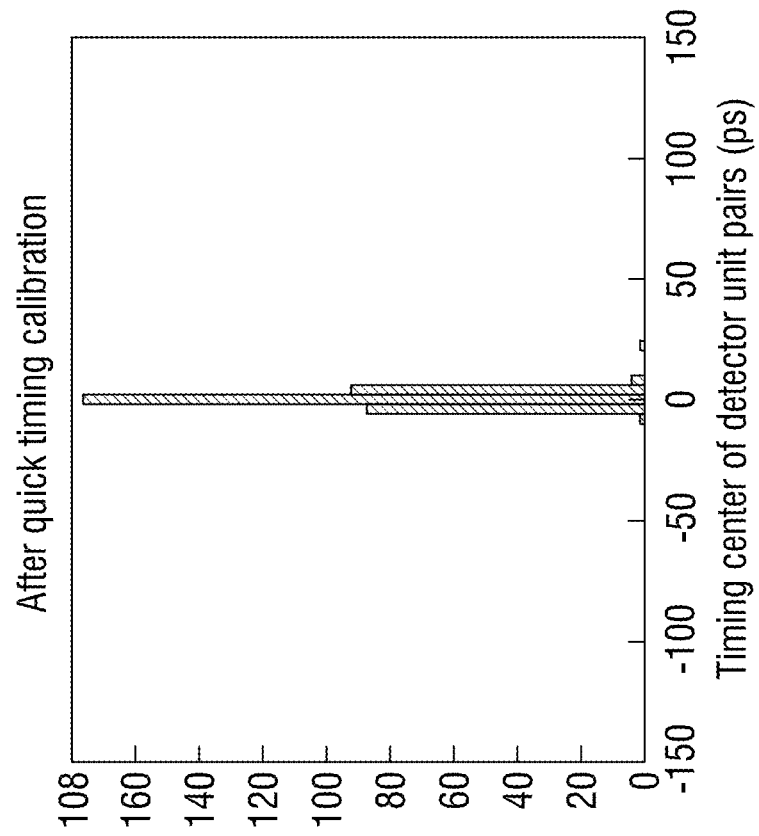
FIG. 15B shows timing offset between DU pairs after quick timing calibration.
Figure 15A:
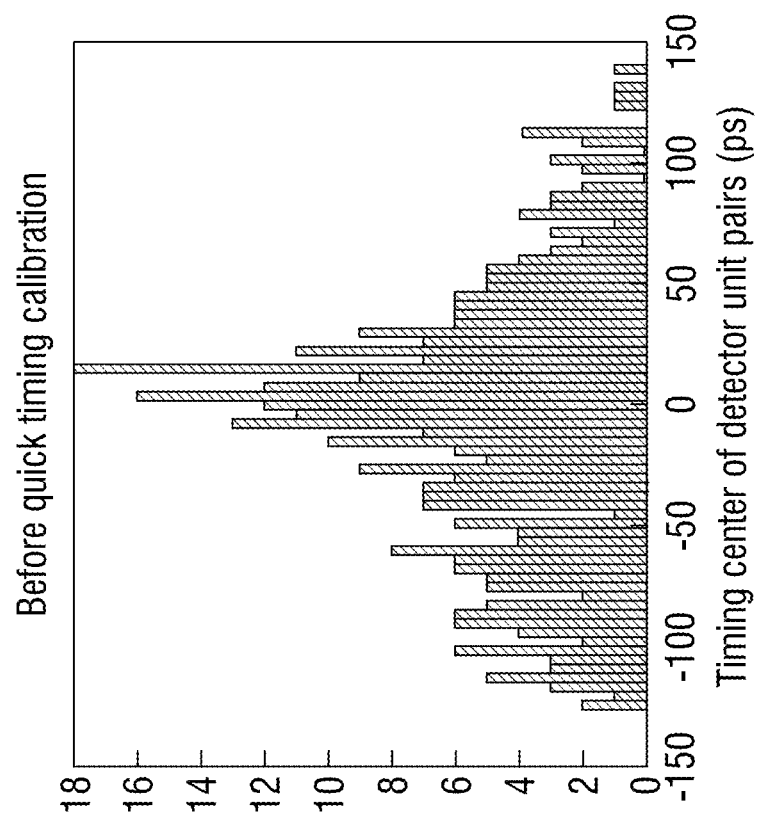
FIG. 15A shows timing offset between DU pairs before quick timing calibration.
Figure 16:
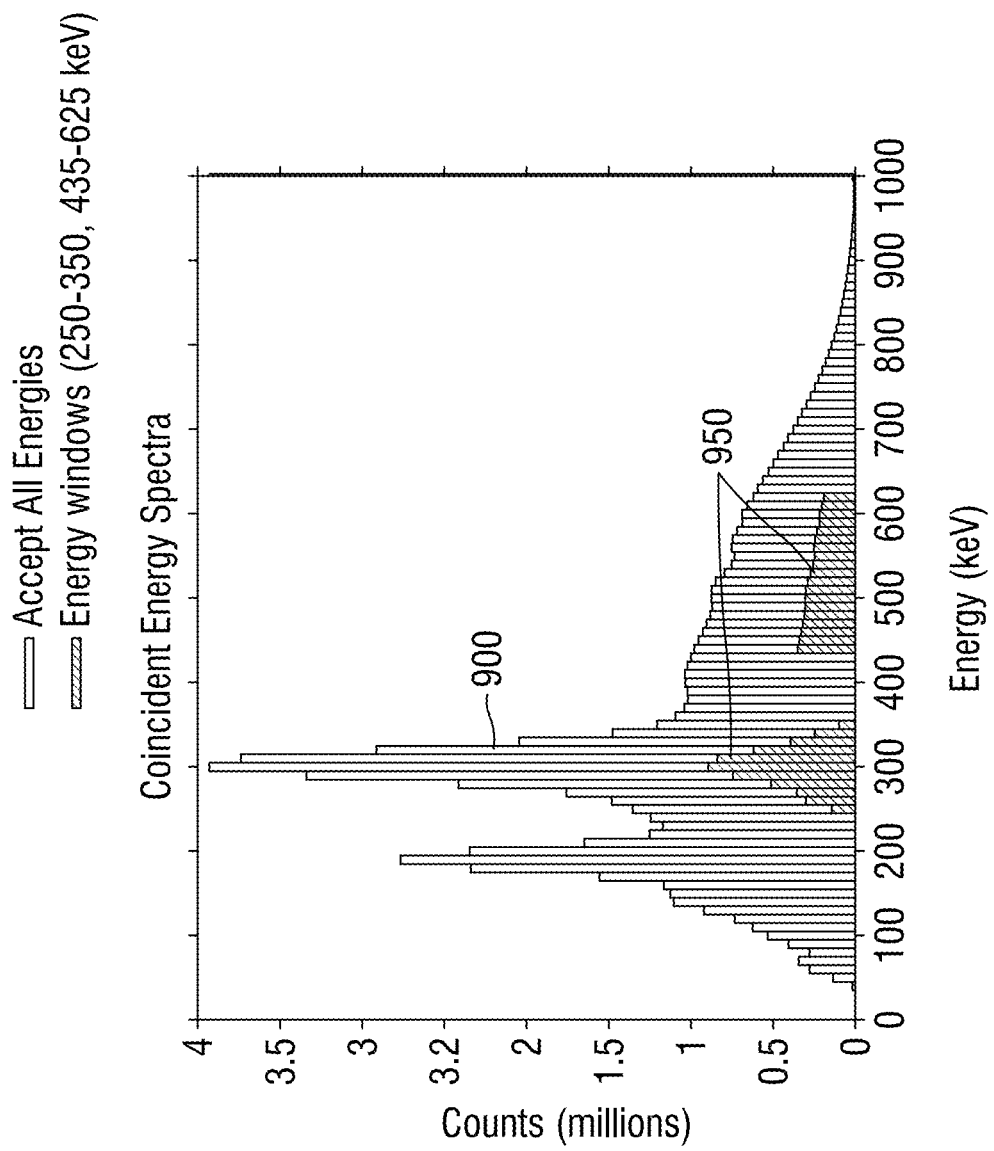
FIG. 16 shows the difference between the counts available when limiting counts by applying an energy window to avoid walk effects and when accepting all counts by performing walk correction.

Timing offset between DU pairs is greatly reduced after quick timing calibration. For example, FIG. 15A shows timing offset between DU pairs before quick timing calibration, and FIG. 15B shows timing offset between DU pairs after quick timing calibration. According to one embodiment discussed herein, an accurate, convenient and fast method for timing calibration for TOF PET scanners is provided.

Various embodiments discussed herein provide good timing resolution in order for a TOF PET scanner to effectively reduce the statistical noise in the reconstructed images to improve the image quality and may be used to maintain accurate timing correction during daily clinical use in order to achieve images for TOF PET scanners with a reduced number of artifacts.

According to one embodiment, timing offset calibration is provided by coupling together all processing units to be calibrated by coincident events.

According to another embodiment, timing offset calibration is provided by coupling together groups of overlapping crystals by coincident gamma photons until a sufficient number of coincident gamma photons between the groups provides sufficient timing offset calibration for all of the crystals.

According to one embodiment, during initial full timing calibration, (1) timing offset and timing walk within DU pairs or DUs are calibrated by placing an limited extent positron-emitting source in the scanner FOV and (2) after correcting for timing offset and timing walk within DU pairs or DUs, timing offset between DU pairs or DUs are calibrated using an internal radiation (e.g., lutetium).

According to one embodiment, in step (1), the limited extent source is preferably thick enough that crystal is coupled to many crystals in the other DU.

According to another embodiment, during daily clinical use, (1) timing offset correction and timing walk correction from initial timing calibration is applied before performing timing calibration during daily clinical use, (2) timing offset per processing unit is calculated using an internal radiation (e.g., lutetium) and an limited extent positron-emitting source in the scanner FOV together, and/or (3) timing offset per processing unit is calibrated using an internal radiation (e.g., lutetium) while a scanner is not in use.

According to two different implementations, (1) data with limited extent positron-emitting source and an internal radiation (e.g., lutetium) are acquired separately, and (2) data with limited extent positron-emitting source an internal radiation (e.g., lutetium) are acquired simultaneously.

Advantageously, at least using a number of embodiments disclosed herein, (1) there is no need to move a radiation source or use large limited extent radiation source during initial full timing calibration; (2) quick timing calibration can be implemented without external radiation source during daily clinical use; (3) a simplified method is provided that does not require position dependent timing correction; and (4) calibration is relatively fast because of parallel processing and the simplified method.

The method and system described herein can be implemented in a number of technologies but generally relate to processing circuitry for performing the calibration described herein. In one embodiment, the processing circuitry is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include a computer processor and having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores. In an embodiment in which neural networks are used, the processing circuitry used to train the artificial neural network need not be the same as the processing circuitry used to implement the trained artificial neural network that performs the calibration described herein. For example, processor circuitry and memory may be used to produce a trained artificial neural network (e.g., as defined by its interconnections and weights), and an FPGA may be used to implement the trained artificial neural network. Moreover, the training and use of a trained artificial neural network may use a serial implementation or a parallel implementation for increased performance (e.g., by implementing the trained neural network on a parallel processor architecture such as a graphics processor architecture).

Numerous modifications and variations of the embodiments presented herein are possible in light of the above teachings. It is therefore to be understood that within the scope of the claims, the disclosure may be practiced otherwise than as specifically described herein.

The invention claimed is:

1. A method of performing timing calibration in time of flight (TOF) positron emission tomography (PET), comprising:
    obtaining relative timing offset within each of a plurality of sets of detector units by placing a limited extent annihilation radiation source in a field of view (FOV) of a PET scanner, each set of the plurality of sets of detector units having more than two detector units;
    correcting the relative timing offset within each of the plurality of sets of detector units;
    calibrating a timing offset between the plurality of sets of detector units using an internal radiation; and
    determining a total timing offset as a sum of the corrected relative timing offset within each of the plurality of sets of detector units and the calibrated timing offset between the plurality of sets of detector units.

2. The method according to claim 1, wherein the step of correcting the relative timing offset includes correcting a timing walk.

3. The method according to claim 2, wherein the step of correcting the timing walk includes non-linear timing walk correction.

4. The method according to claim 1, wherein the internal radiation is radiation that results from decay of radioactive material that is part of a scintillator array of the PET scanner.

5. The method according to claim 4, wherein a decay process of the internal radiation includes at least two nearly simultaneous emissions from which coincidence events are formed.

6. The method according to claim 4, wherein a decay process of the internal radiation includes an emission from which coincidence events can be formed from Compton scattering in detectors caused by the emission.

7. The method according to claim 1, wherein the internal radiation is present in at least one of the scintillator, an adhesive holding a reflector in place, the reflector itself, and a detector housing.

8. The method according to claim 1, wherein the internal radiation is Lu-176 or Co-60.

9. The method according to claim 1, wherein the limited extent annihilation radiation source comprises a limited extent source with an extent so that each crystal of the scanner is coupled to many crystals in a particular set of detector units other than the plurality of sets of detector units.

10. The method according to claim 1, wherein the limited extent annihilation radiation source has a narrowest cross-sectional extent of less than 10 mm.

11. The method according to claim 1, wherein the limited extent annihilation radiation source is a line source.

12. The method according to claim 11, wherein the limited extent annihilation radiation source is a positron emitting source.

13. The method according to claim 1, wherein the relative timing offset within each of the plurality of sets of detector units is calculated using neural networks.

14. The method according to claim 1, wherein the limited extent annihilation radiation source is at least one of a Ge-68 line source, a F18-FDG line source or a Na-22 line source.

15. An imaging time of flight (TOF) positron emission tomography (PET) system, comprising:
    a limited extent annihilation radiation source arranged in an imaging region of the imaging system;
    a detector configured to detect coincident event pairs resulting from annihilation of positrons; and
    circuitry configured to perform timing calibration of the TOF PET system by
        obtaining relative timing offset within each of a plurality of set of detector units via the limited extent annihilation radiation source in a field of view (FOV) of the TOF PET scanner, each set of the plurality of sets of detector units having more than two detector units;
        correcting the relative timing offset within each of the plurality of sets of detector units;
        calibrating a timing offset between the plurality of sets of detector units using an internal radiation; and
        determining a total timing offset as a sum of the corrected relative timing offset within each of the plurality of sets of detector units and the calibrated timing offset between the plurality of sets of detector units.

16. The TOF PET system according to claim 15, wherein the correcting the relative timing offset includes correcting a timing walk, which includes a non-linear timing walk correction.

17. The TOF PET system according to claim 15, wherein the circuitry is further configured to obtain a portion of data from the internal radiation and the limited extent annihilation radiation source separately.

18. The TOF PET system according to claim 15, wherein the circuitry is further configured to obtain a portion of data from the internal radiation and the limited extent annihilation radiation source simultaneously.

* * * * *